(12) United States Patent
Gutterer

(10) Patent No.: US 6,410,551 B1
(45) Date of Patent: Jun. 25, 2002

(54) TETRAZOLE DERIVATIVES

(75) Inventor: Beate Gutterer, Allensbach (DE)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/446,703

(22) PCT Filed: Jul. 18, 1998

(86) PCT No.: PCT/EP98/04477

§ 371 (c)(1),
(2), (4) Date: Dec. 23, 1999

(87) PCT Pub. No.: WO99/05111

PCT Pub. Date: Feb. 4, 1999

(30) Foreign Application Priority Data

Jul. 25, 1997 (EP) .............................................. 97112792

(51) Int. Cl.$^7$ ........................ A61K 31/44; C07D 221/06

(52) U.S. Cl. ........................................ 514/290; 546/101

(58) Field of Search ................................. 546/109, 101; 514/290

(56) References Cited

FOREIGN PATENT DOCUMENTS

EP 0 490 823 6/1992

OTHER PUBLICATIONS

Lugnier C et al.; Analysis of the specificity of inhibitors against some cyclic phosphodiesterases by multiparametric techniques; Pharmazie (Pharat 00317144); 92; vol. 47; pp 46–9.

Ca 111:77829 Reference, Assymetric reductive amination of cycloalkanones. VIII. EPC–Synthese of arylsubstituted cis–4aR, 10bR– and cis–4aS, 10bS–octahydrophenanthridines, p. 736, vol. 111, 1989.*

* cited by examiner

*Primary Examiner*—Alan L. Rotman
*Assistant Examiner*—Binta Robinson
(74) *Attorney, Agent, or Firm*—Jacobson Holman, PLLC

(57) ABSTRACT

Compounds of formula I,

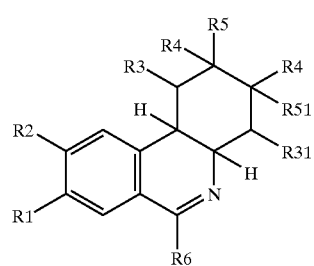

(I)

in which R1, R2, R3, R31, R4, R5, R51 and R6 have the meanings indicated in the description, are efficacious bronchial therapeutics.

24 Claims, No Drawings

TETRAZOLE DERIVATIVES

FIELD OF APPLICATION OF THE INVENTION

The invention relates to novel 6-[(tetrazol-5-yl)-phenyl]phenanthridines, which are used in the pharmaceutical industry for the production of medicaments.

KNOWN TECHNICAL BACKGROUND

Chem. Ber. 1939, 72, 675–677, J. Chem. Soc., 1956, 4280–4283 and J. Chem. Soc. (C), 1971, 1805 describe the synthesis of partial hydrogenated 6-phenylphenanthridines. In the international patent applications WO97/35854 and WO97/28131 partial hydrogenated 6-phenylphenanthridines are described as cyclic nucleotide phosphodiesterase (PDE) inhibitors of type 4.

DESCRIPTION OF THE INVENTION

It has now been found that the novel 6-phenylphenanthridines, which are described below in greater detail, which differ from the prior art, in particular, by the substitution on the 6-phenyl ring, have surprising and particularly advantageous properties.

The invention thus relates to compounds of the formula I

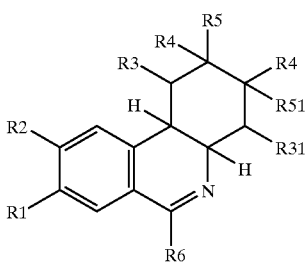

(I)

in which
R1 is hydroxyl, 1–4C-alkoxy, 3–7C-cycloalkoxy, 3–7C-cycloalkylmethoxy or completely or predominantly fluorine-substituted 1–4C-alkoxy,
R2 is hydroxyl, 1–4C-alkoxy, 3–7C-cycloalkoxy, 3–7C-cycloalkylmethoxy or completely or predominantly fluorine-substituted 1–4C-alkoxy,
or in which
R1 and R2 together are a 1–2C-alkylenedioxy group,
R3 is hydrogen or 1–4C-alkyl,
R31 is hydrogen or 1–4C-alkyl,
or in which
R3 and R31 together are a 1–4C-alkylene group,
R4 is hydrogen or 1–4C-alkyl,
R5 is hydrogen,
R51 is hydrogen,
or in which
R5 and R51 together are an additional bond,
R6 is a phenyl radical substituted by R7, where
R7 is a tetrazol-5-yl radical substituted by a radical R8, where
R8 is hydrogen, 1–7C-alkyl, 3–7C-cycloalkyl, 3–7C-cycloalkylmethyl or Ar-1–4C-alkyl, where
Ar is a phenyl radical which is unsubstituted or substituted by R9 and/or R10, and
R9 and R10 independently of one another are halogen, nitro, cyano, 1–4C-alkyl, trifluoromethyl or 1–4C-alkoxy,
and the salts of these compounds.

1–4C-Alkyl represents a straight-chain or branched alkyl radical having 1 to 4 carbon atoms. Examples which may be mentioned are the butyl, isobutyl, sec-butyl, tert-butyl, propyl, isopropyl and, preferably, the ethyl and methyl radicals.

1–4C-Alkoxy represents radicals which, in addition to the oxygen atom, contain a straight-chain or b ranched alkyl radical having 1 to 4 carbon atoms. Examples which may be mentioned are the butoxy, isobutoxy, sec-butoxy, tert-butoxy, propoxy, isopropoxy and, preferably, the ethoxy and methoxy radicals.

3–7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentyl methoxy are preferred.

Completely or predominantly fluorine-substituted 1–4C-alkoxy which may be mentioned are, for example, the 2,2,3,3,3-pentafluoropropoxy, the perfluoroethoxy, the 1,2,2-trifluoroethoxy, in particular the 1,1,2,2-tetrafluoroethoxy, the trifluoromethoxy, the 2,2,2-trifluoroethoxy and, preferably, the difluoromethoxy radicals. "Predominantly" in this connection means that more than half of the hydrogen atoms are substituted by fluorine atoms.

1–2C-Alkylenedioxy represents, for example, the methylenedioxy (—O—$CH_2$—O—) and the ethylenedioxy radicals (—O—$CH_2$—$CH_2$—O—).

If R3 and R31 together have the meaning 1–4C-alkylene, the positions 1 and 4 in compounds of the formula I are linked to one another by a 1–4C-alkylene bridge, 1–4C-alkylene representing straight-chain or branched alkylene radicals having 1 to 4 carbon atoms. Examples which may be mentioned are the radicals methylene (—$CH_2$—), ethylene (—$CH_2$—$CH_2$—), trimethylene (—$CH_2$—$CH_2$—$CH_2$—), 1,2-dimethylethylene [—CH($CH_3$)—CH($CH_3$)—] and isopropylidene [—C($CH_3$)$_2$—].

If R5 and R51 together are an additional bond, then the carbon atoms in positions 2 and 3 in compounds of the formula I are linked to one another via a double bond.

1–7C-Alkyl represents straight-chain or branched alkyl radicals having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

3–7C-Cycloalkyl represents the cyclopropyl, cyclobutyl, cyclopentyl, cyclohexyl and the cycloheptyl radicals. The 5–7C-cycloalkyl radicals cyclopentyl, cyclohexyl and cycloheptyl may be mentioned as preferred.

3–7C-Cycloalkylmethyl represents a methyl radical which is substituted by one of the abovementioned 3–7C-cycloalkyl radicals. Examples which may be mentioned are the cyclopentylmethyl and the cyclohexylmethyl radicals.

Ar-1–4C-alkyl represents one of the abovementioned 1–4C-alkyl radicals, which is substituted by one of the aryl radicals defined above. Examples which may be mentioned are the p-methoxybenzyl, the phenethyl and the benzyl radicals.

Halogen within the meaning of the invention is bromine, chlorine and fluorine.

Suitable salts for compounds of the formula I—depending on substitution—are all acid addition salts or all salts with bases. Particular mention may be made of the pharmacologically tolerable salts of the inorganic and organic acids and bases customarily used in pharmacy. Those which are suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether it is a mono- or polybasic acid and depending on which salt is desired—in an equimolar quantitative ratio or one differing therefrom.

On the other hand—for example if the tetrazol-5-yl radical R7 is substituted by R8=H— salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which may be obtained initially as process products, for example in the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compounds of the formula I to be emphasized are those in which

R1 is 1–4C-alkoxy, 3–7C-cycloalkoxy, 3–7C-cycloalkylmethoxy or completely or predominantly fluorine-substituted 1–2C-alkoxy, R2 is 1–4C-alkoxy, 3–7C-cycloalkoxy, 3–7C-cycloalkylmethoxy or completely or predominantly fluorine-substituted 1–2C-alkoxy, R3 is hydrogen, R31 is hydrogen, or in which R3 and R31 together are a 1–2C-alkylene group, R4 is hydrogen or 1–4C-alkyl, R5 is hydrogen, R51 is hydrogen, or in which R5 and R51 together are an additional bond, R6 is a phenyl radical substituted by R7, where R7 is a tetrazol-5-yl radical substituted by a radical R8, where R8 is hydrogen, 1–7C-alkyl, 3–7C-cycloalkyl, 3–7C-cycloalkylmethyl or Ar-1–4C-alkyl, where Ar is a phenyl radical which is unsubstituted or substituted by R9 and/or R10, and R9 and R10 independently of one another are 1–4C-alkyl or 1–4C-alkoxy, and the salts of these compounds.

Compounds of the formula I particularly to be emphasized are those in which

R1 is 1–4C-alkoxy, 3–7C-cycloalkoxy or completely or predominantly fluorine-substituted 1–2C-alkoxy, R2 is 1–4C-alkoxy, 3–7C-cycloalkoxy or completely or predominantly fluorine-substituted 1–2C-alkoxy, R3 is hydrogen, R31 is hydrogen, or in which R3 and R31 together are a 1–2C-alkylene group, R4 is hydrogen or 1–4C-alkyl, R5 is hydrogen, R51 is hydrogen, or in which R5 and R51 together are an additional bond, R6 is a phenyl radical substituted by R7, where R7 is a tetrazol-5-yl radical substituted by a radical R8, where R8 is hydrogen, 1–4C-alkyl, 5–7C-cycloalkyl, 3–7C-cycloalkylmethyl or Ar-1–2C-alkyl, where Ar is a phenyl radical which is unsubstituted or substituted by R9, and R9 is 1–2C-alkyl or 1–2C-alkoxy, and the salts of these compounds.

Preferred compounds of the formula I are those in which

R1 is 1–4C-alkoxy,

R2 is 1–4C-alkoxy,

R3 is hydrogen,

R31 is hydrogen,

R4 is hydrogen,

R5 is hydrogen,

R51 is hydrogen,

R6 is a phenyl radical substituted by R7, where

R7 is a tetrazol-5-yl radical substituted by R8, where

R8 is hydrogen, 1–4C-alkyl or 4-methoxybenzyl, and the salts of these compounds.

Particularly preferred compounds of the formula I are those in which

R1 is methoxy or ethoxy,

R2 is methoxy or ethoxy,

R3 is hydrogen,

R31 is hydrogen,

R4 is hydrogen,

R5 is hydrogen,

R51 is hydrogen,

R6 is a phenyl radical substituted by R7, where

R7 is a 2H-tetrazol-5-yl radical substituted by R8, where

R8 is hydrogen, ethyl or 4-methoxybenzyl, and the salts of these compounds.

The compounds of the formula I are chiral compounds having chiral centers in the positions 4a and 10b and, depending on the meaning of the substituents R3, R31, R4, R5 and R51, further chiral centers in the positions 1, 2, 3 and 4.

Numbering:

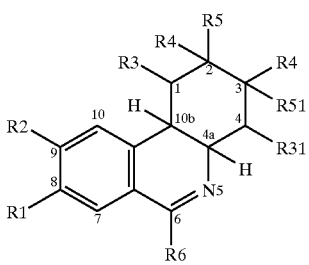
(I)

The invention therefore includes all conceivable pure diastereomers and pure enantiomers and their mixtures in any mixing ratio, including the racemates. The compounds of the formula I are preferred in which the hydrogen atoms in the positions 4a and 10b are cis to one another. Particularly preferred here are the pure cis-diastereomers and the pure cis-enantiomers and their mixtures in any mixing ratio and including the racemates.

The enantiomers can be separated in a manner known per se (for example by preparation and separation of appropriate diastereoisomeric compounds). Preferably, a separation of enantiomers takes place at the stage of the starting compounds of the formula III

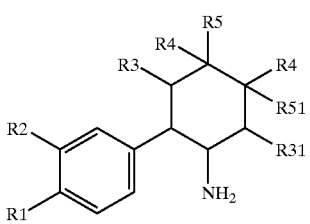
(III)

for example via salt formation of the racemic compounds of the formula III with optically active carboxylic acids. Alternatively, enantiomerically pure starting compounds of the formula III can also be prepared via asymmetric syntheses.

The tetrazol-5-yl radical R7 of the compounds of the formula I can be bonded to the phenyl radical R6 either in the ortho, meta or para position to the phenanthridine ring.

Those compounds of the formula I are preferred in which the tetrazol-5-yl radical R7 is bonded to the phenyl radical R6 in the meta or para position to the phenanthridine ring. The compounds of the formula I in which the tetrazol-5-yl radical R7 is bonded in the para position are particular preferred in this connection.

Compounds of the formula I in which R1, R2, R3, R31, R4, R5, R51, R6 and R7 have the meanings indicated above and R8 is hydrogen occur in 2 tautomeric forms, which are in equilibrium with one another (1H and 2H form of the tetrazol-5-yl radical). The invention therefore includes both tautomeric forms in any mixing ratio.

By bonding of the substituent R8 (R8≠H) to the tetrazol-5-yl group, the conversion of the two tautomeric forms into one another is blocked. The invention therefore also relates to the 1H- and 2H-tetrazol-5-yl compounds of the formula I substituted by a radical R8 (R8≠H), both in pure form and in any mixing ratio. In this connection, the compounds of the formula I are preferred in which the tetrazol-5-yl radical is substituted in the 2 position by one of the radicals R8 (R8≠H).

The invention further relates to a process for the preparation of the compounds of the formula I, in which R1, R2, R3, R31, R4, R5, R51, A and R6 have the meanings indicated above, and their salts.

The Process Comprises a) for the preparation of compounds of the formula I in which R1, R2, R3, R31, R4, R5, R51, R6 and R7 have the meanings indicated above and R8 is hydrogen, reacting corresponding compounds of the formula I, in which R6 is cyanophenyl, with alkali metal azides and halogen salts of ammonia, or b) for the preparation of compounds of the formula I in which R1, R2, R3, R31, R4, R5, R51, R6, R7 and R8 (R8≠H) have the meanings indicated above, cyclocondensing corresponding compounds of the formula II

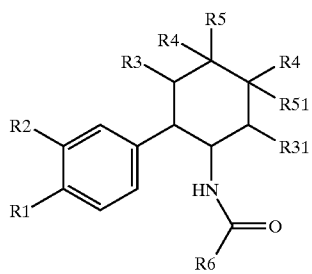
(II)

and,
if desired, then converting the compounds of the formula I obtained according to a) or b) into their salts, or, if desired, then converting salts of the compounds of the formula I obtained according to a) or b) into the free compounds.

If desired, compounds of the formula I obtained can be converted into further compounds of the formula I by derivatization. For example, compounds of the formula I in which R6 is a phenyl radical substituted by R7 and R7 is an unsubstituted 1H- or 2H-tetrazol-5-yl radical can be converted into the corresponding substituted tetrazole compounds of the formula I by alkylation reactions, the hydrogen on the tetrazole ring being replaced by the radicals mentioned for R8—excluding hydrogen. The reactions are expediently carried out analogously to the methods known to the person skilled in the art, e.g. by reaction of the 1H- or 2H-tetrazole compounds of the formula I with compounds of the formula R8-X in the presence of a base, R8 having the abovementioned meanings—excluding hydrogen—and X being a suitable leaving group such as, for example, a chlorine, bromine or iodine atom or an alkylsulfate radical. The 1- and 2-substituted tetrazole regioisomer mixtures usually formed in the alkylation are separated by methods known to the person skilled in the art, such as crystallization or chromatography on suitable support materials. An analogous alkylation of tetrazoles and separation of the regioisomers is described, for example, in J. Med. Chem. 1996, 39, 2354.

The reaction of cyanophenyl derivatives with alkali metal azides and halogen salts of ammonia to give 2-, 3- or 4-(1H- or 2H-tetrazol-5-yl)phenyl derivatives which are unsubstituted in the tetrazole moiety is described, for example, in J. Med. Chem. 1993, 36, 3246.

Cyclocondensation is carried out in a manner known per se to the person skilled in the art according to Bischler-Napieralski (e.g. as described in J. Chem. Soc., 1956, 4280–4282) in the presence of a suitable condensing agent, such as, for example, polyphosphoric acid, phosphorus pentachloride, phosphorus trichloride, phosphorus pentoxide, thionyl chloride or preferably phosphorus oxychloride, in a suitable inert solvent, e.g. in a chlorinated hydrocarbon such as chloroform, or in a cyclic hydrocarbon such as toluene or xylene, or another inert solvent such as acetonitrile, or without further solvent using an excess of condensing agent, preferably at elevated temperature, in particular at the boiling temperature of the solvent or condensing agent used.

Compounds of the formula II, in which R1, R2, R3, R31, R4, R5, R51 and R6 have the meanings indicated above, are accessible from the corresponding compounds of the formula III, in which R1, R2, R3, R31, R4, R5 and R51 have the meanings indicated above, by reaction with compounds of the formula R6-CO—X, in which R6 has the meaning indicated above and X is a suitable leaving group, preferably a chlorine atom. For example, benzoylation is carried out as in the following examples according to the Einhorn process, the Schotten-Baumann variant or as described in J. Chem. Soc. (C), 1971, 1805–1808.

Compounds of the formula R6-CO—X and compounds of the formula III are either known or can be prepared in a known manner.

Compounds of the formula R6-CO—X can be prepared, for example, from the corresponding carboxylic acids R6-COOH, in which R6 has the meaning indicated above, by reaction in a manner familiar to the person skilled in the art.

The compounds R6-COOH, in which R6 has the meaning indicated above, are either known or can be obtained from alkyl 2-, 3- or 4-cyanobenzoates in a manner known to the person skilled in the art, e.g. by reaction with alkali metal azides and halogen salts of ammonia to give alkyl 2-, 3- or 4-(1H- or 2H-tetrazol-5-yl)benzoates which are unsubstituted in the tetrazole moiety. Such a reaction is described, for example, in J. Med. Chem. 1993, 36, 3246. If desired, these intermediates can be converted by alkylation with compounds of the formula R8-X in the presence of a base—as described above for the 1H- or 2H-tetrazole compounds of the formula I or in the abovementioned literature—into alkyl R6-carboxylates, in which R6 is a phenyl radical substituted by R7, R7 is a 1H- or 2H-tetrazol-5-yl radical substituted by a radical R8 and R8 is not hydrogen, but has one of the other abovementioned meanings for R8. By means of alkaline or acidic hydrolysis conditions familiar to the person skilled in the art, the alkyl R6-carboxylates are converted into the free carboxylic acids R6-COOH.

The compounds of the formula III can be prepared, for example, from compounds of the formula IV

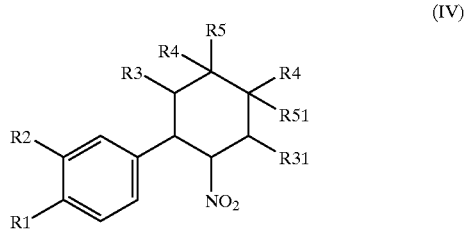

(IV)

in which R1, R2, R3, R31, R4, R5 and R51 have the meanings mentioned above, by reduction of the nitro group.

Reduction is carried out in a manner known to the person skilled in the art, for example as described in J. Org. Chem. 1962, 27, 4426 or as described in the following examples. Preferably, reduction is carried out by catalytic hydrogenation, e.g. in the presence of Raney nickel, in a lower alcohol such as methanol or ethanol at room temperature and under normal or elevated pressure. If desired, a catalytic amount of an acid, such as, for example, hydrochloric acid, can be added to the solvent.

The compounds of the formula III, in which R1, R2, R3, R31 and R4 have the meanings indicated above and R5 and R51 together are an additional bond, can be prepared from the corresponding compounds of the formula IV by selective reduction of the nitro group in a manner known to the person skilled in the art, for example in the presence of Raney nickel in a lower alcohol as a solvent using hydrazine hydrate as a hydrogen donor.

The compounds of the formula IV, in which R1, R2, R3, R31 and R4 have the meanings indicated above and R5 and R51 are hydrogen, are either known or can be prepared from corresponding compounds of the formula IV, in which R5 and R51 together are an additional bond. The reaction can be carried out in a manner known to the person skilled in the art, preferably by hydrogenation in the presence of a catalyst, such as, for example, palladium on activated carbon, e.g. as described in J. Chem. Soc. (C), 1971, 1805–1808.

The compounds of the formula IV, in which R5 and R51 together are an additional bond, are either known or can be obtained by reaction of compounds of the formula V

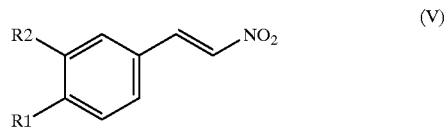

(V)

in which R1 and R2 have the abovementioned meanings, with compounds of the formula VI

R3-CH=C(R4)—C(R4)=CH—R31 (VI)

in which R3, R31 and R4 have the abovementioned meanings. Cycloaddition is carried out here in a manner known to the person skilled in the art according to Diels-Alder, e.g. as described in J. Amer. Chem. Soc. 1957, 79, 6559 or in J. Org. Chem. 1952, 17, 581 or as described in the following examples.

Compounds of the formula IV obtained in the cycloaddition, in which the phenyl ring and the nitro group are trans to one another, can be converted into the corresponding cis compounds in a manner known to the person skilled in the art, e.g. as described in J. Amer. Chem. Soc. 1957, 79, 6559 or as described in the following examples.

The compounds of the formula V and VI are either known or can be prepared in a known manner. The compounds of the formula V can be prepared, for example, from corresponding compounds of the formula VII in a manner known to the person skilled in the art, as described, for example, in J. Chem. Soc. 1951, 2524 or in J. Org. Chem. 1944, 9, 170 or as in the following examples.

The compounds of the formula VII

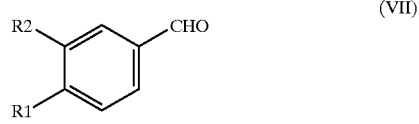

(VII)

in which R1 and R2 have the meanings indicated above, are either known or can be prepared in a manner known to the person skilled in the art, as described, for example, in Ber. Dtsch. Chem. Ges. 1925, 58, 203.

The isolation and purification of the substances according to the invention are carried out in a manner known per se, for example by distilling off the solvent in vacuo and recrystallizing the resulting residue from a suitable solvent or subjecting it to one of the customary purification methods, such as, for example column chromatography on suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol), which contains the desired acid or base, or to which the desired acid or base is then added. The salts are obtained by filtering, reprecipitation, precipitation with a nonsolvent for the addition salt or by evaporation of the solvent. Salts obtained can be converted by alkalization or by acidification into the free compounds, which in turn can be converted into salts. In this manner, pharmacologically intolerable salts can be converted into pharmacologically tolerable salts.

The following examples serve to explain the invention in greater detail without restricting it. Likewise, further compounds of the formula I whose preparation is not described explicitly can be prepared in an analogous manner or in a manner familiar to the person skilled in the art using customary process techniques.

In the examples, m.p. stands for melting point, h for hour(s), RT for room temperature, EF for empirical formula, MW for molecular weight, calc. for calculated, fnd for found. The compounds and their salts mentioned in the examples are a preferred subject of the invention.

EXAMPLES

Final Products 1. (+/−)-cis-9-Ethoxy-8-methoxy-6-[4-(2H-tetrazol-5-yl) phenyl]-1,2,3,4,4a,10b-hexahydrophenanthridine 4.2 g of (+/−)-cis-9-ethoxy-8-methoxy-6-(4-cyanophenyl)-1,2,3,4,4a,10b-hexahydrophenanthridine (compound A1), 0.65 g of ammonium chloride and 0.83 g of sodium azide are suspended in 150 ml of abs. dimethylformamide and heated at 120° C. for 24 h. The reaction mixture is partitioned between water and diethyl ether, and the organic phase is dried with sodium sulfate and concentrated. The residue is chromatographed on silica gel using methylene chloride/methanol in the ratio 4/1. After concentration of the corresponding eluate fractions, the title compound is obtained as a solidified oil.

EF: $C_{23}H_{25}N_5O_2$; MW 403.48; Elemental; analysis×0.7 $H_2O$: calc.: C, 66.39 H, 6.40 N, 16.83. fnd: C, 66.34 H, 6.46 N, 16.45.

2. (+/−)-cis-9-Ethoxy-8-methoxy-6-[4-(2ethyl-2H-tetrazol-5-yl)phenyl]-1,2,3,4,4a,10b-hexahydrophenanthridine 3.55 g of (+/−)-cis-N-[2-(3-ethoxy-4-methoxyphenyl)-cyclohexyl]-4-(2-ethyl-2H-tetrazol-5-yl)benzanamide (compound A2) are dissolved in 150 ml of acetonitrile and 1.0 ml of phosphorus oxychloride and the solution is stirred at 80° C. overnight. The reaction mixture is treated with 60 ml of ethyl acetate and extracted with sodium hydrogencarbonate solution. The organic phase is dried using sodium sulfate and concentrated. The residue is extracted by stirring with ethyl acetate/petroleum ether in the ratio 1/1, filtered off with suction and dried. 2.06 g of the title compound of m.p. 167–170° C. are obtained.

EF: $C_{25}H_{29}N_5O_2$; MW 431.54. Elemental analysis: calc.: C, 69.58 H, 6.77 N, 16.23. fnd.: C, 69.50 H, 6.92 N, 16.38.

Starting from starting compounds described below, the following is obtained according to the procedure in Example 2:

3. (+/−)-cis-9-Ethoxy-8-methoxy-6-[4-(2-p-methoxybenzyl-2H-tetrazol-5-yl)phenyl]-1,2,3,4,4a,10b-hexahydrophenanthridine M.p.: solidified oil; EF: $C_{31}H_{33}N_5O_3$; MW 523.62; Elemental; analysis×0.3 $H_2O$: calc.: C, 70.38 H, 6.40 N, 13.24; fnd.: C, 70.67 H, 6.57 N, 12.97;

4. (−)-cis-8,9-Dimethoxy-6-[4-(2ethyl-2H-tetrazol-5-yl) phenyl]-1,2,3,4,4a,10b-hexahydrophenanthridine M.p.: solidified oil; EF: $C_{24}H_{27}N_5O_2$; MW 417.52; Elemental; analysis×0.12 $H_2O$: calc.: C, 68.62 H, 6.55 N, 16.67; fnd.: C, 68.63 H, 6.81 N, 16.59.

Specific rotation: $[\alpha]_D^{20}=-75.20°$ (c=2, ethanol).

Starting Compounds

A1. (+/−)-cis-9-Ethoxy-8-methoxy-6-[4-cyanophenyl]-1,2,3,4,4a,10b-hexahydrophenanthridine 5.1 g of (+/−)-cis-N-[2-(3-ethoxy-4-methoxyphenyl)-cyclohexyl]-4-cyanobenzamide (compound A5) are dissolved in 100 ml of acetonitrile and 3 ml of phosphorus oxychloride and the solution is stirred at 50° C. for 8 h. The reaction mixture is added to 100 ml of saturated sodium hydrogencarbonate solution and extracted with ethyl acetate. The organic phase is washed with sodium hydrogencarbonate solution and water, dried using sodium sulfate and concentrated. 4.3 g of the title compound are obtained as solidified oil.

A2. (+/−)-cis-N-[2-(3-Ethoxy4-methoxyphenyl)-cyclohexyl]4-(2-ethyl-2H-tetrazol4-yl)benzamide 5.0 g of (+/−)-cis-2-ethoxy-1-methoxy-4-(2-aminocyclohexyl)benzene (compound B1) are dissolved in 60 ml of methylene chloride and 5.3 ml of triethylamine. A solution of 7.4 g of 4-(2-ethyl-2H-tetrazol-5-yl)benzoyl chloride in 60 ml of methylene chloride is added dropwise at RT, and the mixture is extracted after stirring overnight with 100 ml each of water, 2N hydrochloric acid, saturated sodium hydrogencarbonate solution and water again. The organic phase is dried using sodium sulfate and concentrated. The residue is chromatographed on silica gel using a mixture of toluene/dioxane in the ratio 10/1. After concentration of the product fractions, 3.6 g of the title compound of m.p. 157–159°C. are obtained.

Starting from starting compounds described below, the following is obtained according to the procedure described in Example A2:

A3. (+/−)-cis-N-[2-(3-Ethoxy-4-methoxyphenyl)-cyclohexyl]-4-(2-p-methoxybenzyl-2H-tetrazol-5-yl)benzamide M.p.: 176–179° C.

A4. (−)-cis-N-[2-(3,4-Dimethoxyphenyl)cyclhexyl]-4-(2-ethyl-2H-tetrazol-5-yl)benzamide M.p. solidified oil; Optical rotation: $[\alpha]_D^{20}=-195.5°$ (c=0.2, ethanol).

A5. (+/−)cis-N-2-[3-Ethoxy-4-methoxyphenyl)cyclohexyl]-4-cyanobenzamide

M.p. solidified oil.

B1. (+/−)-cis-2-Ethoxy-1-methoxy-4-(2-aminocyclohexyl) benzene 40.0 g of (+/−)-cis-2-ethoxy-1-methoxy-4-(2-nitrocyclohex-4-enyl)benzene (compound C1) are dissolved in 1000 ml of ethanol and 500 ml of tetrahydrofuran, treated with 10 g of Raney nickel and hydrogenated at a hydrogen pressure of 100 bar for 4 days in an autoclave. After filtration and removal of the solvent in vacuo, 35.9 g of the title compound are obtained as a solidifying oil.

B2. (+/−)-cis-1,2-Dimethoxy-4-(2-aminocyclohexyl) benzene 8.5 g of (+/−)-cis-1,2-dimethoxy-4-(2-nitrocyclohexyl) benzene are dissolved in 400 ml of methanol and treated with 7 ml of hydrazine hydrate and 2.5 g of Raney nickel in portions at RT in the course of 8 h. After stirring overnight at RT, the reaction mixture is filtered, the filtrate is concentrated and the residue is chromatographed on silica gel using a mixture of toluene/ethyl acetate/triethylamine=4/2/0.5. The title compound is obtained as an oil.

B3. (−)-cis-1,2-Dimethoxy-4-(2-aminocyclohexyl)benzene 12.0 g of (+/−)-cis-1,2-dimethoxy-4-(2-aminocyclohexyl)benzene an d 6.2 g of (−)-mandelic acid are dissolved in 420 ml of dioxane and 60 ml of tetrahydrofuran and the solution is stirred at RT overnight. The solid is filtered off with suction, dried, treated with 100 ml of saturated sodium hydrogencarbonate solution and extracted with ethyl acetate. The organic phase is dried using sodium sulfate and concentrated under reduced pressure. 4.8 g of the title compound of m.p.: 80–81.5° C. are obtained.

Specific rotation: $[\alpha]_D^{20}$=−58.50° (c=1, ethanol)

C1. (+/−)-cis-2-Ethoxy-1-methoxy4-(2-nitrocyclohex-4-enyl)benzene 89.25 g of (+/−)-trans-2-ethoxy-1-methoxy-4-(2-nitrocyclohex-4-enyl)benzene (compound D1) and 37 g of potassium hydroxide are dissolved in 500 ml of absolute ethanol. A solution of 23.5 ml of conc. sulfuric acid in 120 ml of absolute ethanol is then added dropwise such that the internal temperature does not exceed −2° C. After stirring for 1 h, the mixture is added to 4 l of ice water, and the precipitate is filtered off with suction, washed with water and dried. M.p.: 66–67° C.

C2. (+/−)-cis-1,2-Dimethoxy-4-(2-nitrocyclohex-4-enyl)benzene 10.0 g of (+/−)-trans-1,2-dimethoxy-4-(2-nitrocyclohex-4-enyl)benzene and 20.0 g of potassium hydroxide are dissolved in 150 ml of ethanol and 35 ml of dimethyl formamide. A solution of 17.5 ml of conc. sulfuric acid in 60 ml of ethanol is then added dropwise such that the internal temperature does not exceed 4° C. After stirring for 1 h, the mixture is added to 1 l of ice water, the precipitate is filtered off with suction, washed with water and dried, and the crude product is recrystallized from ethanol. 8.6 g of the title compound of m.p. 82.5–84° C. are obtained.

C3. (+/−)-cis-1,2-Dimethoxy-4-(2-nitrocyclohexyl)benzene 8,4 g of (+/−)-cis-1,2-dimethoxy-4-(2-nitrocyclohex-4-enyl)benzene are dissolved in 450 ml of methanol, treated with 2 ml of conc. hydrochloric acid and hydrogenated after addition of 500 mg of 10% strength Pd/C. The reaction mixture is filtered and the filtrate is concentrated. M.p.: 84–86.5° C.

D1. (+/−)-trans-2-Ethoxy-1-methoxy4-(2-nitrocyclohex4-enyl)benzene 110 g of 3-ethoxy-2-methoxy-ω-nitrostyrene (compound E1) and 360 mg of hydroquinone are suspended in 360 ml of absolute toluene and treated at −70° C. with 180 ml of liquid 1,3-butadiene. The mixture is stirred at 160–180° C. for 6 days in an autoclave and then cooled. The product is extracted by stirring with ethanol, filtered off with suction and dried. M.p.: 130–131° C.

D2. (+/−)-trans-1,2-Dimethoxy 4-(2-nitrocyclohex-4-enyl)benzene 50.0 g of 3,4-dimethoxy-ω-nitrostyrene and 1.0 g (9.1 mmol) of hydroquinone are suspended in 200 ml of abs. toluene and treated at −70° C. with 55.0 g (1.02 mmol) of liquid 1,3-butadiene. The mixture is stirred at 160° C. for 6 days in an autoclave and then cooled. Some of the solvent is removed on a rotary evaporator, and the resulting precipitate is filtered off with suction and recrystallized in ethanol.

M.p.: 113.5–115.5° C.

E1. 3-Ethoxy-2-methoxy-ω-nitrostyrene 236 g of 3-ethoxy-2-methoxybenzaldehyde, 101 g of ammonium acetate and 320 ml of nitromethane are heated to 100° C. for 4 h in 655 ml of glacial acetic acid. The solution is added to 5 l of ice water, and the precipitate is filtered off with suction, washed with water and dried. M.p.: 132–133° C.

E2. 3.4-Dimethoxyy-ω-nitrostyrene 207.0 g of 3,4-dimethoxybenzaldehyde, 100.0 g of ammonium acetate and 125 ml of nitromethane are heated to boiling for 3–4 h in 1.0 l of glacial acetic acid. After cooling in an ice bath, the precipitate is filtered off with suction, rinsed with glacial acetic acid and petroleum ether and dried. M.p.: 140–141° C. Yield: 179.0 g.

Commercial Utility

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones; and also illnesses of the central nervous system, such as depressions or arteriosclerotic dementia.

The invention further relates to a method for the treatment of mammals, including humans, which are suffering from one of the abovementioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of medicaments which are employed for the treatment and/or prophylaxis of the illnesses mentioned.

The invention furthermore relates to medicaments for the treatment and/or prophylaxis of the illnesses mentioned, which contain one or more of the compounds according to the invention.

The medicaments are prepared by processes which are known per se and familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar with auxiliaries which are suitable for the desired pharmaceutical formulations on account of his expert knowledge. In addition to solvents, gel formers, ointment bases and other active compound excipients, for example antioxidants, dispersants, emulsifiers, preservatives, solubilizers or permeation promoters, can be used.

For the treatment of disorders of the respiratory tract, the compounds according to the invention are preferably also administered by inhalation. To do this, these are either administered directly as a powder (preferably in micronized form) or by atomizing solutions or suspensions which contain them. With respect to the preparations and administration forms, reference is made, for example, to the details in European Patent 163 965.

For the treatment of dermatoses, the compounds according to the invention are in particular administered in the form of those medicaments which are suitable for topical application. For the production of the medicaments, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The medicaments according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1–99%. The dose for administration by inhalation is customarly between 0.1 and 3 mg per day. The customary dose in the case of systemic therapy (p.o. or i.v.) is between 0.03 and 3 mg/kg per day.

Biological Investigations

In the investigation of PDE 4 inhibition on the cellular plane, the activation of inflammatory cells is ascribed particular importance. An example is FMLP (N-formyl-methionyl-leucyl-phenylalanine) induced superoxide production of neutrophilic granulocytes, which can be measured as luminolamplified chemilumines cence. (Mc Phail L C, M Strum S L, Leone P A and Sozzani S, The neutrophil respiratory burst mechanism. In "Immunology Series" 57: 47–76, 1992; ed. Coffey R G (Marcel Decker, Inc., New York-Basel-Hong Kong)).

Substances which inhibit chemiluminescence and cytokine secretion and the secretion of proinflammatory mediators on inflammatory cells, in particular neutrophilic and eosinophilic granulocytes, T-lymphocytes, monocytes and macrophages are those which inhibit PDE 4. This isoenzyme of the phosphodiesterase families is particularly represented in granulocytes. Its inhibition leads to an increase in the intracellular cyclic AMP concentration and thus to the inhibition of cellular activation. PDE 4 inhibition by the substances according to the invention is thus a central indicator for the suppression of inflammatory processes. (Giembycz M A, Could isoenzyme-selective phosphodiesterase inhibitors render bronchodilatory therapy redundant in the treatment of bronchial asthma?. Biochem Pharmacol 43: 2041–2051, 1992; Torphy T J et al., Phosphodiesterase inhibitors: new opportunities for treatment of asthma. Thorax 46: 512–523, 1991; Schudt C et al., Zardaverine: a cyclic AMP PDE 3/4 inhibitor. In "New Drugs for Asthma Therapy", 379–402, Birkhäuser Verlag Basel 1991; Schudt C et al., Influence of selective phosphodiesterase inhibitors on human neutrophil functions and levels of cAMP and Ca; Naunyn-Schmiedebergs Arch Pharmacol 344; 682–690, 1991; Tenor H and Schudt C, Analysis of PDE isoenzyme profiles in cells and tissues by pharmacological methods. In "Phophodiesterase Inhibitors", 21–40, "The Handbook of Immunopharmacology", Academic Press, 1996; Hatzelmann A et al., Enzymatic and functional aspects of dual-selective PDE3/4-Inhibitors. In "Phosphodiesterase Inhibitors", 147–160. "The Handbook of Immunopharmacology", Academic Press, 1996.

1. Inhibition of PDE 4 Activity

Methodology

The activity test was carried out by the method of Bauer and Schwabe, which was adapted to microtiter plates (Naunyn-Schmiedeberg's Arch. Pharmacol. 1980, 311, 193–198). In this connection, the PDE reaction is carried out in the first step. In a second step, the resultant 5'-nucleotide is cleaved to give the uncharged nucleoside by a 5'-nucleotidase of the snake venom from Crotalus atrox. In the third step, the nucleoside is separated from the remaining charged substrate on ion exchange columns. The columns are eluted with 2 ml of 30 mM ammonium formate (pH 6.0) directly into minivials to which 2 ml of scintilation fluid is additionally added for counting.

The inhibitory values determined for the compounds according to the invention [inhibitory concentration as -log $IC_{50}$ (mol/l)] follow from Table A below, in which the numbers of the compounds correspond to the numbers of the examples.

TABLE A

Inhibition of the PDE 4 activity

| Compound | −log IC$_{50}$ |
|---|---|
| 2 | 8.78 |

What is claimed is:

1. A compound of formula I

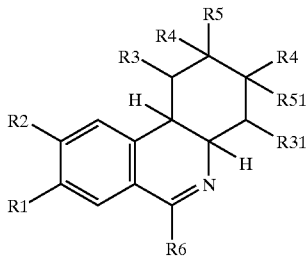

(I)

in which
R1 is hydroxyl, 1–4C-alkoxy, 3–7C-cycloalkoxy, 3–7C-cycloalkylmethoxy or completely or predominantly fluorine-substituted 1–4C-alkoxy,
R2 is hydroxyl, 1–4C-alkoxy, 3–7C-cycloalkoxy, 3–7C-cycloalkylmethoxy or completely or predominantly fluorine-substituted 1–4C-alkoxy,
or in which
R1 and R2 together are a 1–2C-alkylenedioxy group,
R3 is hydrogen or 1–4C-alkyl,
R31 is hydrogen or 1–4C-alkyl,
or in which
R3 and R31 together are a 1–4C-alkylene group,
R4 is hydrogen or 1–4C-alkyl,
R5 is hydrogen,
R51 is hydrogen,
or in which
R5 and R51 together are an additional bond,
R6 is a phenyl radical substituted by R7, where
R7 is a tetrazol-5-yl radical substituted by a radical R8, where
R8 is hydrogen, 1–7C-alkyl, 3–7C-cycloalkyl, 3–7C-cycloalkylmethyl or Ar-1–4C-alkyl, where
Ar is a phenyl radical which is unsubstituted or substituted by R9 and/or R10, and
R9 and R10 independently of one another are halogen, nitro, cyano, 1–4C-alkyl, trifluoromethyl or 1–4C-alkoxy,
or a salt thereof.

2. A compound of formula I as claimed in claim 1, in which
R1 is 1–4C-alkoxy, 3–7C-cycloalkoxy, 3–7C-cycloalkylmethoxy or completely or predominantly fluorine-substituted 1–2C-alkoxy,
R2 is 1–4C-alkoxy, 3–7C-cycloalkoxy, 3–7C-cycloalkylmethoxy or completely or predominantly fluorine-substituted 1–2C-alkoxy,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is a phenyl radical substituted by R7, where
R7 is a tetrazol-5-yl radical substituted by a radical R8, where
R8 is hydrogen, 1–7C-alkyl, 3–7C-cycloalkyl, 3–7C-cycloalkylmethyl or Ar-1–4C-alkyl, where
Ar is a phenyl radical which is unsubstituted or substituted by R9 and/or R10, and
R9 and R10 independently of one another are 1–4C-alkyl or 1–4C-alkoxy,
or a salt thereof.

3. A compound of formula I as claimed in claim 1, in which
R1 is 1–4C-alkoxy, 3–7C-cycloalkoxy or completely or predominantly fluorine-substituted 1–2C-alkoxy,
R2 is 1–4C-alkoxy, 3–7C-cycloalkoxy or completely or predominantly fluorine-substituted 1–2C-alkoxy,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is a phenyl radical substituted by R7, where
R7 is a tetrazol-5-yl radical substituted by a radical R8, where
R8 is hydrogen, 1–4C-alkyl, 5–7C-cycloalkyl, 3–7C-cycloalkylmethyl or Ar-1–2C-alkyl, where
Ar is a phenyl radical which is unsubstituted or substituted by R9, and
R9 is 1–2C-alkyl or 1–2C-alkoxy,
or a salt thereof.

4. A compound of formula I as claimed in claim 1, in which
R1 is 1–4C-alkoxy,
R2 is 1–4C-alkoxy,
R3 is hydrogen,
R31 is hydrogen,
R4 is hydrogen,
R5 is hydrogen,
R51 is hydrogen,
R6 is a phenyl radical substituted by R7, where
R7 is a tetrazol-5-yl radical substituted by R8, where
R8 is hydrogen, 1–4C-alkyl or 4-methoxybenzyl,
or a salt thereof.

5. A compound of formula I as claimed in claim 1, in which
R1 is methoxy or ethoxy,
R2 is methoxy or ethoxy,
R3 is hydrogen,
R31 is hydrogen,
R4 is hydrogen,
R5 is hydrogen, R51 is hydrogen,
R6 is a phenyl radical substituted by R7, where
R7 is a 2H-tetrazol-5-yl radical substituted by R8, where
R8 is hydrogen, ethyl or 4-methoxybenzyl,
or a salt thereof.

6. In a method for treating a subject afflicted with a condition amenable to treatment with an active ingredient which is a phosphodiesterase inhibitor and which comprises administering to the subject an effective amount of the active ingredient, the improvement wherein said active ingredient is a compound of formula I, as claimed in claim 1, or a pharmaceutically-acceptable salt thereof.

7. A medicament composition comprising a compound of formula I as claimed in claim 1, or a pharmaceutically-acceptable salt thereof, together with a pharmaceutical auxiliary and/or excipient.

8. A method for producing a medicament composition by combining an active ingredient for treating an airway disorder with a suitable pharmaceutical auxiliary and/or excipient, wherein the active ingredient is a compound of formula I as claimed in claim 1 or a pharmaceutically-acceptable salt thereof.

9. A compound of formula I as claimed in claim 1, in which
R1 is hydroxyl or 1–4C-alkoxy,
R2 is hydroxyl or 1–4C-alkoxy,
R3 is hydrogen or 1–4C-alkyl,
R31 is hydrogen or 1–4C-alkyl,
R4 is hydrogen or 1–4C-alkyl,
R5 is hydrogen,
R51 is hydrogen,
R6 is a phenyl radical substituted by R7, where
R7 is a tetrazol-5-yl radical substituted by a radical R8, where
R8 is hydrogen or 1–7C-alkyl,
or a salt thereof.

10. A compound of formula I as claimed in claim 4, in which R8 is 1–4C-alkyl, or a salt thereof.

11. A compound of formula I as claimed in claim 10, in which R7 is a 2H-tetrazol-5-yl radical substituted by R8, where R8 is 1–4C-alkyl, or a salt thereof.

12. A compound of formula I as claimed in claim 11, in which R8 is 2-ethyl,
or a salt thereof.

13. A compound of formula I

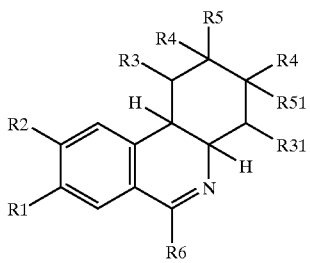

(I)

in which
R1 is 1–4C-alkoxy,
R2 is 1–4C-alkoxy,
R3 is hydrogen,
R31 is hydrogen,
R4 is hydrogen R5 is hydrogen
R51 is hydrogen
R6 is a phenyl radical substituted by R7, where
R7 is a tetrazol-5-yl radical substituted by a radical R8, where
R8 is hydrogen, 1–7C-alkyl, 3–7C-cycloalkyl, 3–7C-cycloalkylmethyl or Ar-1–4C-alkyl, where
Ar is a phenyl radical which is unsubstituted or substituted by R9 and/or R10, and
R9 and R10 independently of one another are halogen, nitro, cyano, 1–4C-alkyl, trifluromethyl or 1–4C-alkoxy,
or a salt thereof.

14. A compound according to claim 13 wherein the salt is a pharmaceutically acceptable salt.

15. In a method of treating a subject afflicted with a condition amenable to treatment with an active ingredient which is a phosphodiesterase inhibitor and which comprises administering to the subject an effective amount of the active ingredient, the improvement wherein said active ingredient is a compound of formula I, as claimed in claim 13, or a pharmaceutically acceptable salt thereof.

16. A medicament composition comprising a compound of formula I as claimed in claim 13, or a pharmaceutically acceptable salt thereof, together with a pharmaceutical auxiliary and/or excipient.

17. A method of producing a medicament composition by combining an active ingredient for treating an airway disorder with a suitable pharmaceutical auxiliary and/or excipient, wherein the active ingredient is a compound of formula I as claimed in claim 13, or a pharmaceutically acceptable salt thereof.

18. A compound of formula I as claimed in claim 13, in which
R1 is 1–4C-alkoxy,
R2 is 1–4C-alkoxy,
R3 is hydrogen,
R31 is hydrogen,
R4 is hydrogen
R5 is hydrogen
R51 is hydrogen
R6 is a phenyl radical substituted by R7, where
R7 is a tetrazol-5-yl radical substituted by a radical R8, where
R8 is 1–7C-alkyl,
or a salt thereof.

19. A compound of formula I as claimed in claim 13, in which
R1 is 1–4C-alkoxy,
R2 is 1–4C-alkoxy,
R3 is hydrogen,
R31 is hydrogen,
R4 is hydrogen
R5 is hydrogen
R51 is hydrogen
R6 is a phenyl radical substituted by R7, where
R7 is a tetrazol-5-yl radical substituted by a radical R8, where
R8 is hydrogen, 1–4C-alkyl or 4-methoxybenzyl,
or a salt thereof.

20. A compound of formula I as claimed in claim 19, in which
R8 is 1–4C-alkyl,
or a salt thereof.

21. A compound of formula I as claimed in claim 20, in which R7 is a 2H-tetrazol-5-yl radical substituted by R8, where R8 is 1–4C-alkyl, or a salt thereof.

22. A compound of formula I as claimed in claim 21, in which

R8 is 2-ethyl, or a salt thereof.

23. A compound of formula I as claimed in claim 13, in which

R1 is 1–4C-alkoxy,

R2 is 1–4C-alkoxy,

R3 is hydrogen,

R31 is hydrogen,

R4 is hydrogen,

R5 is hydrogen,

R51 is hydrogen,

R6 is a phenyl radical substituted by R7, where

R7 is a tetrazol-5-yl radical substituted by a radical R8, where

R8 is hydrogen, 1–7C-alkyl, 3–7C-cycloalkyl, 3–7C-cycloalkylmethyl or Ar-1–4C-alkyl, where Ar is a phenyl radical which is unsubstituted or substituted by R9 and/or R10, and R9 and R10 independently of one another are 1–4C-alkyl or 1–4C-alkoxy, or a salt thereof.

24. A compound of formula I as claimed in claim 13, in which

R1 is 1–4C-alkoxy,

R2 is 1–4C-alkoxy,

R3 is hydrogen,

R31 is hydrogen,

R4 is hydrogen

R5 is hydrogen

R51 is hydrogen

R6 is a phenyl radical substituted by R7, where

R7 is a tetrazol-5-yl radical substituted by a radical R8, where

R8 is hydrogen, 1–4C-alkyl, 5–7C-cycloalkyl, 3–7C-cycloalkylmethyl or Ar-1–2C-alkyl, where Ar is a phenyl radical which is unsubstituted or substituted by R9, and R9 is 1–2C-alkyl or 1–2C-alkoxy, or a salt thereof.

\* \* \* \* \*